(12) United States Patent
Day

(10) Patent No.: US 7,015,021 B2
(45) Date of Patent: Mar. 21, 2006

(54) METHOD FOR MAKING PURIFIED PLASMINOGEN ACTIVATOR-INHIBITOR TYPE 1 (PAI-1) AND PURIFIED PAI-1 MADE THEREFROM

(75) Inventor: Duane D. Day, Novi, MI (US)

(73) Assignee: Molecular Innovations, Inc., Southfield, MI (US)

( * ) Notice: Subject to any disclaimer, the term of this patent is extended or adjusted under 35 U.S.C. 154(b) by 379 days.

(21) Appl. No.: 10/370,828

(22) Filed: Feb. 20, 2003

(65) Prior Publication Data

US 2003/0180925 A1      Sep. 25, 2003

Related U.S. Application Data

(60) Provisional application No. 60/367,286, filed on Mar. 25, 2002.

(51) Int. Cl.
*C12N 9/99*         (2006.01)

(52) U.S. Cl. ...................................... 435/184; 514/836
(58) Field of Classification Search ..................... None
See application file for complete search history.

(56) References Cited

U.S. PATENT DOCUMENTS

| 5,866,413 A | 2/1999 | Sambrook et al. ....... 435/320.1 |
| 6,103,498 A | 8/2000 | Lawrence et al. ......... 435/69.2 |

OTHER PUBLICATIONS

Arroya De Prada N, Schroeck F, Sinner EK, Muehlenweg B, Twellmeyer J, Sperl S, Wilhelm OG, Schmitt M, Magdolen V (2002). Interaction of plasminogen activator inhibitor type-1 (PAI-1) with vitronectin. *Eur J Biochem* 269(1):184-192.
Muehlenweg B, Sperl S, Magdolen V, Schmitt M, Harbeck N (2001). Interference with the urokinase plasminogen activator system: a promising therapy concept for solid tumors. *Expert Opin. Biol. Ther.* 4:683-691.
Berkenpas MB, Lawrence DA, Ginsberg D (1995). Molecular evolution of plasminogen activator inhibitor-1 functional stability. *EMBO J* 14(13):2969-2977.
Lawrence DA, Ginsburg D (1995). Plasminogen Activator Inhibitors. In: Molecular Biology of Thrombosis and Hemostasis, Roberts HR et al., (Eds.), Marcel Dekker Inc., New York, Chapter 25, pp. 517-543.
Lawrence DA, Olson ST, Palaniappan S, Ginsburg D (1994). Engineering plasminogen activator inhibitor 1 mutants with increased functional stability. *Biochemistry* 33(12):3643-3648.
Angles-Cano E, Gris JC, Loyau S, Schved JF (1993). Familial association of high levels of histidine-rich glycoprotein and plasminogen activator inhibitor-1 with venous thromboembolism. *J Lab Clin Med* 121(5):646-653.

Kassis J, Hirsh J, Podor TJ (1992). Evidence that postoperative fibrinolytic shutdown is mediated by plasma factors that stimulate endothelial cell I plasminogen activator inhibitor biosynthesis. *Blood* 80(7):1758-1764.
Ridker PM, Vaughan DE, Stampfer MJ, Manson JE, Shen C, Newcomer LM, Goldhaber SZ, Hennekens CH (1992). Baseline fibrinolytic state and the risk of future venous thrombosis. A prospective study of endogenous tissue-type plasminogen activator and plasminogen activator inhibitor. *Circulation* 85(5):1822-1827.
Sherman PM, Lawrence DA, Yang AY, Vandenberg ET, Paielli D, Olson ST, Shore JD, Ginsburg D (1992). Saturation mutagenesis of the plasminogen activator inhibitor-1 reactive center. *J. Biol. Chem.* 267(11):7588-7595.
Ellis V, Dano K (1991). Plasminogen activation by receptor-bound urokinase. *Semin Thromb Hemost* 17(3):194-200.
Plow EF, Felez J, Miles LA (1991). Cellular regulation of fibrinolysis. *Thromb Haemost* 66(1):32-36.
Pollanen J, Stephens RW, Vaheri A (1991). Directed plasminogen activation at the surface of normal and malignant cells. *Adv Cancer Res* 57:273-328.
Erickson LA, Fici GJ, Lund JE, Boyle TP, Polites HG, Marotti KR (1990). Development of venous occlusions in mice transgenic for the plasminogen activator inhibitor-1 gene. *Nature* 346(6279):74-76.
Hajjar KA, Hamel NM (1990). Identification and characterization of human endothelial cell membrane binding sites for tissue plasminogen activator and urokinase. *J Biol Chem* 265(5):2908-2916.
Reilly TM, Seetharam R, Duke JL, Davis GL, Pierce SK, Walton HL, Kingsley D, Sisk WP (1990). Purification and characterization of recombinant plasminogen activator inhibitor-1 from *Escherichia coli*. *J Bio Chem* 265(16): 9570-9574.
Lawrence D, Strandberg L, Grundstrom T, Ny T (1989). Purification of active human plasminogen activator inhibitor 1 from *Escherichia coli*. Comparison with natural and recombinant forms purified from eucaryotic cells. *Eur J Biochem* 186(3):523-533.
Lindahl T, Wiman B (1989). Purification of high and low molecular weight plasminogen activator inhibitor 1 from fibrosarcoma cell-line HT 1080 conditioned medium. *Biochim Biophys Acta* 994(3):253-257.

(Continued)

*Primary Examiner*—Bruce R. Campell
*Assistant Examiner*—B. Dell Chism
(74) *Attorney, Agent, or Firm*—Fitzpatrick, Cella, Harper & Scinto

(57) ABSTRACT

The present disclosure relates to a single step method for purifying PAI-1, PAI-1 fragments and PAI-1 mutants using a metal chelate resin. The disclosure further relates to the purified PAI-1 obtained by the disclosed method and uses for the purified PAI-1.

7 Claims, 6 Drawing Sheets

OTHER PUBLICATIONS

Wun TC, Palmier MO, Siegel NR, Smith CE (1989). Affinity purification of active plasminogen activator inhibitor-1 (PAI-1) using immobilized anhydrourokinase. Demonstration of the binding, stabilization, and activation of PAI-1 by vitronectin. *J Biol Chem* 264(14):7862-7868.

Alessi MC, Declerck PJ, De Mol M, Nelles L, Collen D (1988). Purification and characterization of natural and recombinant human plasminogen activator inhibitor-1 (PAI-1). *Eur. J. Biochem* 175(3):531-540.

Aznar J, Estelles A, Tormo G, Sapena P, Tormo V, Blanch S, Espana F (1988). Plasminogen activator inhibitor activity and other fibrinolytic variables in patients with coronary artery disease. *Br Heart J* 59(5):535-541.

Hsueh AJW, Liu YX, Cajander SB, Ny T (1988). Molecular mechanisms in the hormonal regulation of plasminogen activator activity in ovarian granulosa cells and cumulus-oocyte complexes. In: Haseltine FP et al, eds, "Meiotic Inhibition: Molecular Control of Meiosis." New York: Liss, pp. 227-258.

Moscatelli D, Rifkin MR (1988). Membrane and matrix localization of proteinases: a common theme in tumor cell invasion and angiogenesis. *Biochim Biophys Acta* 948(1):67-85.

Saksela O, Rifkin DB (1988). Cell-associated plasminogen activation: regulation and physiological functions. *Annu Rev Cell Biol* 4:93-126.

Hekman CM, Loskutoff DJ (1988). Bovine plasminogen activator inhibitor 1: specificity determinations and comparison of the active, latent, and guanidine-activated forms. *Biochemistry* 27(8):2911-2918.

Levin EG, Santell L (1987). Conversion of the active to latent plasminogen activator inhibitor from human endothelial cells. *Blood* 70(4):1090-1098.

Dano K, Andreasen PA, Grondahl-Hansen J, Kristensen P, Nielsen LS, Skriver L (1985). Plasminogen activators, tissue degradation, and cancer. *Adv Cancer Res* 44:139-266.

Hamsten A, Wiman B, de Faire U, Blomback M (1985). Increased plasma levels of a rapid inhibitor of tissue plasminogen activator in young survivors of myocardial infarction. *N Engl J Med* 313(25):1557-1563.

Hekman CM, Loskutoff DJ (1985). Endothelial cells produce a latent inhibitor of plasminogen activators that can be activated by denaturants. *J Biol Chem* 260(21):11581-11587.

Kluft C, Verheijen JH, Jie AF, Rijken DC, Preston FE, Sue-Ling HM, Jespersen J, Aasen AO (1985). The postoperative fibrinolytic shutdown: a rapidly reverting acute phase pattern for the fast-acting inhibitor of tissue-type plasminogen activator after trauma. *Scand J Clin Lab Invest* 45(7):605-610.

Nilsson IM, Ljungner H, Tengborn L (1985). Two different mechanisms in patients with venous thrombosis and defective fibrinolysis: low concentration of plasminogen activator or increased concentration of plasminogen activator inhibitor. *Br Med J* 290(6480):1453-1456.

Paramo JA, Colucci M, Collen D, van de Werf F (1985). Plasminogen activator inhibitor in the blood of patients with coronary artery disease. *Br Med J* 291(6495):573-574.

Saksela O (1985). Plasminogen activation and regulation of pericellular proteolysis. *Biochim Biophys Acta* 823(1):35-65.

Wiman B, Ljungberg B, Chmielewska J, Urden G, Blomback M, Johnsson H (1985). The role of the fibrinolytic system in deep vein thrombosis. *J Lab Clin Med* 105(2):265-270.

Juhan-Vague I, Moerman B, De Cock F, Aillaud MF, Collen D (1984). Plasma levels of a specific inhibitor of tissue-type plasminogen activator (and urokinase) in normal and pathological conditions. *Thromb Res* 33(5):523-530.

van Mourik JA, Lawrence DA, Loskutoff DJ (1984). Purification of an inhibitor of plasminogen activator (antiactivator) synthesized by endothelial cells. *J Biol Chem* 259(23):14914-14921.

Hoylaerts M, Rijken DC, Lijnen HR, Collen D (1982). Kinetics of the activation of plasminogen by human tissue plasminogen activator. Role of fibrin. *J Biol Chem* 257(6):2912-2919.

Lane 1  crude E. coli lysate
Lane 2  Column eluant
Lane 3  PAI-1 eluted with 100 mM Imidazole

METHOD FOR MAKING PURIFIED PLASMINOGEN ACTIVATOR-INHIBITOR TYPE 1 (PAI-1) AND PURIFIED PAI-1 MADE THEREFROM

CROSS REFERENCE TO RELATED APPLICATIONS

This application claims priority under 35 U.S.C. § 119(e) to Provisional Application No. 60/367,286, filed Mar. 25, 2002.

FIELD OF THE INVENTION

This invention relates to a method for purifying plasminogen activator inhibitor-1 (PAI-1) by metal chelate affinity chromatography. The invention further relates to compositions made by the method.

BACKGROUND OF THE INVENTION

Various attempts have been made to purify PAI-1, mutants of PAI-1 and fragments thereof. However, these attempts have required multiple chromatographic steps and/or alteration of the protein, e.g. insertion of a 6 histidine tag at the n-terminus, to achieve efficient purification.

Plasminogen activators (PAs) are specific serine proteinases that activate the proenzyme plasminogen, by cleavage of a single Arg-Val peptide bond, to the enzyme plasmin (Saksela O, Biochim Biophys Acta (1985) 823:35–65). Two plasminogen activators are found in mammals, tissue-type PA (tPA) and urokinase-type PA (uPA) (Saksela O et al, Annu Rev Cell Biol (1988) 4:93–126). These enzymes are thought to critically influence many biological processes, including vascular fibrinolysis (Bachmann E, Thromb Haemost (1987) 10:227–265), ovulation (Hsuch A J W et al, In: Haseltine FP et al, eds, "Meiotic Inhibition: Molecular Control of Meiosis" New York: Liss 1988:227–258), inflammation (Pollanen J et al., Adv Cancer Res (1991) 57:273–328), tumor metastasis (Dano K et al., Adv Cancer Res (1985) 44:139–266), angiogenesis (Moscatelli D et al., Biochim Biophys Acta (1988) 948:67–85), and tissue remodeling (Saksela, Annu Rev Cell Biol (1988) 4:93–126).

The regulation of PAs is a complex process controlled on many levels. The synthesis and release of PAs are governed by various hormones, growth factors, and cytokines (Saksela, Annu Rev Cell Biol (1988) 4:93–126; Dano et al., Adv Cancer Res (1985) 44:139–266). Following secretion, PA activity can be regulated both positively and negatively by a number of specific protein-protein interactions. Activity can be enhanced or concentrated by interactions with fibrin (Hoylaerts M et al., J Biol Chem (1982) 257:2912–2919), the uPA receptor (uPAR) (Ellis V et al., Semin Thromb Hemost (1991) 17:194–200), the tPA receptor (tPAR) (Hajjar K A et al., J Biol Chem (1990) 265:2908–2916), or the plasminogen receptor (Plow E F et al., Thromb Haemost (1991) 66:32–36).

PA activity can be down regulated by specific PA inhibitors (PAIs) (Lawrence, D. A et al., In: Molecular Biology of Thrombosis and Hemostasis, Roberts, H. R. et al., (Eds.), Marcel Dekker Inc., New York, chapter 25, pp. 517–543 (1995). The PAIs have become recognized as critical regulators of the PA system. Four kinetically relevant PAIs are currently recognized: PAI type 1 (PAI-1), initially described as the endothelial cell PAI; PAI type 2 (PAI-2), also referred to as placental PAI; PAI type 3 (PAI-3), also known as activated protein C (APC) inhibitor and proteinase nexin 1 (PN-1), also called glia-derived neurite-promoting factor.

PAI-1 is considered one of the principal regulators of the PA system. It is a single chain glycoprotein with a molecular weight of 50 kDa (Van Mourik J A et al., J Biol Chem (1984) 259:14914–14921) and is the most efficient inhibitor known of the single- and two-chain forms of tPA and of uPA (Table 1) (Lawrence D et al., Eur J Biochem (1989) 186:523–533). PAI-1 also inhibits plasmin and trypsin (Hekman C M et al., Biochemistry (1988) 27:2911–2918) and also inhibits thrombin and activated protein C, though with much lower efficiency.

PAI-1 exists in an active form as it is produced by cells and secreted into the culture medium and an inactive or latent form that accumulates in the culture medium over time (Hekman C M et al., J Biol Chem (1985) 260:11581–11587; Levin E G et al., Blood (1987) 70:1090–1098). The active form spontaneously converts to the latent form with a half-life of about 1 h at 37° C. (Lawrence et al., Eur J Biochem (1985) 186:526–533; Hekman et al., Biochemistry (1988) 27:2911–2918; Levin E G et al. (1987) Blood 70:1090–1098).

The latent form can be converted into the active form by treatment with denaturants, negatively charged phospholipids or Vn (Hekman et al. Biochemistry (1988) 27:2911–2918; Wun T-C et al, J Biol Chem (1989) 264: 7862–7868). The reversible interconversion between the active and latent structures, presumably due to a conformational change, is a unique feature of PAI-1 as compared to other serpins. The latent form appears to be more energetically favored.

Increased levels of circulating PAI-1 are associated with thrombotic disease, including myocardial infarction and deep vein thrombosis (Juhan-Vague I et al., Thromb Res (1984) 33:523–530; Hamsten A et al., N Engl J Med (1985) 313:1557–1563; Wiman B et al., J Lab Clin Med (1985) 105:265–270; Paramo J A et al., BMJ (1985) 291:573–574; Nilsson I M et al., BMJ (1985) 290:1453–1456; Aznar J et al., Br Heart J (1988) 59:535–541; Angles-Cano E et al., J Lab Clin Med (1993) 121-:646–653). Reduced postoperative fibrinolytic activity has been correlated with increased PAI-1 activity immediately following surgery (Kluft C et al., Scand J Clin Lab Invest (1985) 45:605–610), apparently mediated by a plasma factor that stimulates PAI-1 production and secretion from vascular ECs (Kassis J et al., Blood (1992) 80:1758–1764). Consistent with these observations, the overproduction of PAI-1 in transgenic mice results in venous thrombosis primarily in the extremities (Erickson L A et al., Nature (1990) 346:74–76). In contrast, a prospective study found no correlation between PAI-1 levels and vascular disease (Ridker P M et al., Circulation (1992) 85:1822–1827).

There is evidence that the PA system with its key components uPA, its cell surface receptor uPAR and its inhibitor, PAI-1 plays a key role in tumor invasion and metastasis. Structure based design has led to the generation of mutant PAIs which are very selective and are useful for controlling tumor invasion and metastasis. Wilex et al., 2001, Expert Opin. Biol. Ther. 4:693.

U.S. Pat. No. 6,103,498 ("the '498 patent") of Lawrence et al. (incorporated herein by reference) describes mutants of PAI-1 that have been shown to interact with and inhibit elastase and to inhibit vitronectin-associated cell migration. Because of the role of elastase in emphysema, cystic fibrosis (CF) and in acute respiratory distress syndrome (ARDS) in both adults and infants, the '498 patent indicates that the disclosed mutants of PAI-1 are useful for treating these diseases and any other diseases associated with the pathogenic activation of elastase. Lawrence et al. (*Biochemistry* (1994) 33:3643; incorporated herein by reference) also have generated mutants of PAI-1 which have a shorter half life when compared to wild-type PAI-1 but retain wild-type activity. In addition, Sherman et al. (*J. Biol. Chem.* (1992) 267:7588–7595; incorporated herein by reference) have generated mutants of PAI-1 to investigate the role of the reactive center residues of PAI-1 and showed that some of the mutants were inactive, some had a greater preference for uPA and some had a greater preference for tPA than wild-type PAI-1.

U.S. Pat. No. 5,866,413 of Sambrook et al. ("the '413 patent"; incorporated herein by reference) describes PAI-1 mutants which are capable of binding to mutant serine proteases which have become resistant to inhibition by wild-type PAI-1. These mutant PAI-1s may be useful for treating diseases linked to the mutant serine proteases. The '413 patent indicates that the PAI-1 mutants may be useful for inhibiting a mutated t-PA in a patient treated for a thrombotic disorder during an invasive procedure.

The importance of PAI-1 and fragments and mutants of PAI-1 as therapeutic compounds is increasingly being acknowledged. It is therefore desirable to purify PAI-1, PAI-1 mutants and fragments thereof to high purity and in large amounts for therapeutic use. Several purification schemes have been described, many of which require several steps to achieve high purity. It is often the case that purification schemes which require several steps can compromise the activity of the protein that is being purified.

Lindahl and Wiman (*Biochim Biophys Acta* (1989) 23:994) describe a method for purifying high and low molecular weight PAI-1 from fibrosarcoma cell-line HT 1080 which includes an affinity chromatography step (heparin-sepharose), a gel filtration step (Sephadex G-150) and then another affinity chromatography step (resin comprising a monoclonal antibody towards PAI-1).

Wun et al. (*J. Biol. Chem.* (1989) 264:7862–7868) describe an affinity purification of PAI-1 using a resin including an immobilized anhydrourokinase. PAI-1 was purified from both Human Hep G2 hepatoma cells and HT 1080 cells. The PAI-1 purified from the Hep G2 cells was bound to Vn and it was found to be four fold more active than PAI-1 purified from the HT 1080 cells which was not bound to Vn.

Alessi et al. (*Eur. J. Biochem* (1988) 175:531–540) describe a three step procedure for purifying both endogenous and recombinant PAI-1 which includes a zinc-chelate-Sepharose step, a gel filtration step using Sephacryl S-300 and immunoadsorption on an insolubilized murine monoclonal antibody. The recovery was about 20%. The gel filtration step is required to separate an active high molecular weight fraction of PAI-1 (which is in the void volume of the column) from an inactive low molecular weight fraction of PAI-1.

In addition, PAI-1 has been purified through the use of an n-terminal six histidine (His6) tag. See Arroya De Prada et al., *Eur J Biochem* 269:184–192 (2002). N-terminal 6 histidine tags are routinely added to proteins in order to facilitate purification. Arroya de Prada et al. engineered ten different PAI-1 variants, as well as wild-type PAI-1, the previously described PAI-1 mutant Q123K, and another serpin, PAI-2, were recombinantly produced in *Escherichia coli* to include a N-terminal His6 tag and purified by affinity chromatography using a nickel chelating column. Even in the presence of the His6 tag, after a single purification step using the nickel chelating column, the protein was only moderately purified. A second purification step using the nickel chelating column was necessary to achieve >95% purity.

Reilly et al. describe a purification scheme for PAI-1 which includes utilization of sequential anion exchange and cation exchange chromatography on Q-sepharose and S-sepharose columns, with a resultant specific activity of 250,000 units/mg based on its ability to inhibit the enzymatic activity of a single-chain tissue plasminogen activator. See Reilly et al., *J. Biol. Chem.* 265:9570–9574 (1990). A one step purification scheme for recombinant PAI-1 from *E. coli* is described by Sancho et al. using an ion exchange resin, CM-50 Sephadex, with a resultant activity of 132,000 units/ml or 14,666 units/mg.

Although other methods of purifying PAI-1 have been described, these methods are either cumbersome and involve multiple steps or require alteration of the protein to include a purification tag. It is desirable to provide a simple purification method for PAI-1 which allows for efficient purification while not requiring the alteration of the protein for the purpose of purification.

SUMMARY OF THE INVENTION

The present invention relates to a method for preparing PAI-1 in a highly active, and highly purified form in a single step. Any PAI-1 capable of binding divalent metals can be purified according to the method of the present invention. The method is founded upon the surprising discovery that PAI-1 can be highly purified using a metal chelate resin, preferably a cobalt, nickel or zinc resin.

The invention further relates to the highly purified, active PAI-1 purified by the method of the present invention. The method is useful for preparing purified PAI-1, such as any PAI-1 capable of binding to divalent metals, including but not limited to, wild-type PAI-1, mutants of PAI-1, and fragments of both wild-type and mutant PAI-1.

FIGURES

The present invention may be better understood with reference to the attached figures in which—

DETAILED DESCRIPTION OF THE INVENTION

Figure 1:
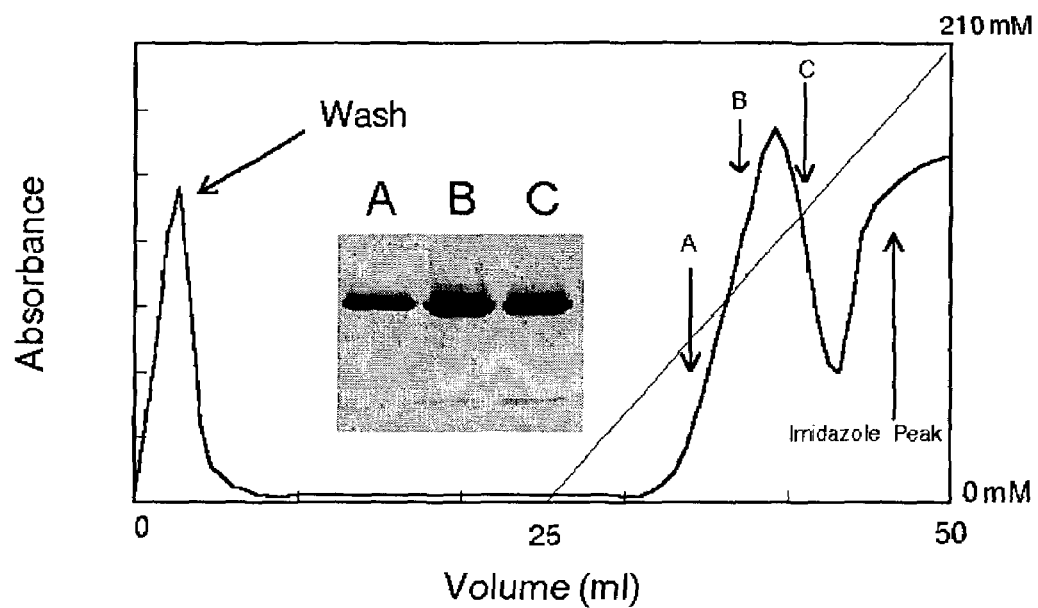
FIG. 1 is a graph showing the elution profile of 14-1b mutant PAI-1 from a cobalt HiTrap™ metal chelating column and further showing SDS-PAGE gel electrophoresis of fractions A, B and C from the major elution peak.

The present invention relates to a method of making purified PAI-1 comprising subjecting unpurified PAI-1 to a solid support which comprises a divalent metal and eluting the PAI-1 from the resin to produce the purified PAI-1, wherein the PAI-1 does not have a six histidine (His6) tag. The purified PAI-1 is from about 70% to about 100% pure and the divalent metal is preferably selected from the group consisting of cobalt, nickel and zinc. In a preferred embodiment the purified PAI-1 is from about 85% to about 98% pure.

The invention is based, at least in part, on the surprising discovery that unpurified PAI-1 which does not have a His6 tag can be efficiently purified by metal chelating chromatography. While additional chromatography steps may be included in the purification, a single purification step comprising metal chelating chromatography results in 70–100% pure PAI-1.

According to the present invention, any unpurified PAI-1 capable of binding a divalent metal can be purified according to the method of the present invention. Preferably, the unpurified PAI-1 does not comprise a His6 tag and can still be purified by the method of the present invention. Such unpurified PAI-1s that can be purified by the method of the present invention include wild-type PAI-1, mutants of PAI-1, such as those mutants described by Wilex et al., 2001, *Expert Opin. Biol. Ther.* 4:693; Lawrence et al. in U.S. Pat. No. 6,103,498; Sambrook et al. in U.S. Pat. No. 5,866,413; Lawrence et al. (*Biochemistry* 33:3643 (1994)); and Sherman et al. (*J. Biol. Chem.* 267:7588–7595 (1992), fragments of wild-type and mutant PAI-1, as well as chemical derivatives of PAI-1, such as those described in U.S. Pat. No. 6,103,498. PAI-1 from any species may be purified using the method of the present invention, so long as the PAI-1 is capable of binding a divalent metal. PAI-1 isolated from Rat does not appear to be capable of binding a divalent metal. In a preferred embodiment, the PAI-1 or mutant PAI-1 (or fragments thereof) which is purified by the present method is of human origin. A number of mutants have been purified using the methods of the present invention. For example, 14-1b PAI-1, which has four mutations and is described by Berkenpas, Lawrence & Ginsberg, 1995, *EMBO Journal* 14:2969–2977, has been purified by the present invention (see Examples below). In addition, the inflammatory mutants described in U.S. Pat. No. 6,103,498 have also been purified using the method of the present invention, e.g. mutants having a single mutations at the P1 residue (Arg 346) which was changed to either Phe or Val. In addition, the T333R mutant was purified according to the present invention. When it was desired to have the purest PAI-1 possible, for example to reduce endotoxin, additional chromatography steps were employed, such as heparin sepharose (affinity chromatography) and phenyl sepharose (hydrophobic interaction chromatography).

The method of the present invention allows for the purification of PAI-1 from any source, including cell lysates from endogenous PAI-1 and recombinant PAI-1 expressed in eukaryotic or prokaryotic expression systems. In addition, PAI-1 may be purified from in vitro biochemical reactions, such as binding reactions, inhibition reactions and in vitro translation reactions. Particularly preferred expression systems for making PAI-1 include *E. coli*.

Cellular extracts may be prepared by methods known to those skilled in the art. Methods for expressing recombinant proteins and for making cellular extracts from both prokaryotic and eukaryotic expression systems are described by Sambrook et al. (2001) Molecular Cloning: A Laboratory Manual, 3$^{rd}$ Edition, Cold Spring Harbor Laboratory Press, Cold Spring Harbor, N.Y.; and Ausubel et al. (1988, updated quarterly) Current Protocols in Molecular Biology, John Wiley & Sons, New York, N.Y.

The unpurified PAI-1 may be purified by subjecting the unpurified PAI-1 (which may be in the form of a cellular extract from endogenous PAI-1 or recombinant PAI-1, in secreted form, together with other constituents, such as protein, RNA, DNA, from a biochemical reaction, such as an in vitro translation reaction, etc.) to any solid support comprising a divalent metal, such as, but not limited to, a metal chelate resin. Qiagen (Hilden, Germany) manufactures and sells a metal chelate resin which can be charged with a divalent metal, such as cobalt, nickel, zinc, copper and manganese, and also provides detailed instructions for purification using the resin. Valen Biotech, Inc. (Atlanta, Ga.) manufactures and sells pre-packed metal chelating resins, called IMAC resins which may also be charged with a divalent metal, such as cobalt, nickel, zinc, copper and manganese. In addition, Amersham Pharmacia Biotech, Inc. (Piscataway, N.J.) manufactures and sells metal chelate resins, such as HiTrap™ Chelating HP, which were used in the present invention (see Example 2 below). In addition, BD Biosciences Clontech (Palo Alto, Calif.) manufactures and sells Talon resins which were used in the present invention (see Example 2 below).

After subjecting the PAI-1 to the solid support comprising a divalent metal, the support can be washed with a buffer to remove unbound materials. The buffer may include a small amount of divalent metal, such as 0.1% nickel or imidazole to ensure that even weakly bound impurities are removed. The purified PAI-1 may then be eluted from the solid support using a buffer containing divalent metal or containing imidazole. The unpurified PAI-1 may also be subjected to the solid support comprising the divalent metal in the presence of a small amount of divalent metal or imidazole in order to ensure that impurities, which may weakly bind to the solid support, do not bind.

Accordingly, the present invention provides a method for making purified PAI-1 which consists essentially of subjecting unpurified PAI-1 to a solid support comprising a divalent metal and eluting the bound PAI-1 from the solid support to produce the purified PAI-1. In a preferred embodiment, the purified PAI-1 is from about 70% to about 100% pure, as shown by coomassie staining or silver staining an SDS-acrylamide gel having the purified PAI-1 therein. Preferably the purified PAI-1 is 85% pure, as shown by coomassie staining or silver staining an SDS-acrylamide gel having the purified PAI-1 therein.

The method may further comprise using addition purification devices, such as, but not limited to dialyzation, gel filtration, ion exchange, affinity chromatography, hydrophobic chromatography; etc. Such devices may be utilized to further improve the purity of the PAI-1, to change the buffer and to further concentrate the PAI-1.

In a preferred embodiment, the PAI-1 is purified using metal chelating affinity chromatography, wherein the metal is selected from the group consisting of cobalt, nickel and zinc. In a particularly preferred embodiment, the metal is cobalt.

The purified PAI-1 made by the method of the present invention is useful for in vitro studies as well as in vivo animal studies. In addition, purified PAI-1 of the present invention may be particularly useful in the treatment of human subjects. As used herein, the term "treating" refers to the administering to subjects of a pharmaceutical composition comprising the purified PAI-1 of the present invention for inhibiting elastase or inhibiting Vn-dependent cell migration and subsequent proliferation, which inhibition may prevent, ameliorate or cure any of a number of diseases described herein.

The pharmaceutical compositions of the present invention wherein the purified PAI-1 protein of the present invention is combined with pharmaceutically acceptable excipient or carrier, may be administered by any means known in the art to achieve the intended purpose. Amounts and regimens for administration can be determined readily by those with ordinary skill in the clinical art of treating any of the particular diseases. Preferred amounts are described below.

Administration may be by parenteral, subcutaneous (sc), intravenous (iv), intramuscular, intraperitoneal, transdermal, topical or inhalation routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the purified PAI-1 of the present invention is contained in an amount effective to achieve its intended purpose. While individual needs vary, determination of optimal ranges of effective amounts of each component is within the skill of the art. Typical dosages comprise 0.1 to 100 mg/kg/body weight, though more preferred dosages are described for certain particular uses, below.

As stated above, in addition to the pharmacologically active protein, the new pharmaceutical preparations may contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

Included in the scope of this invention are salts of the purified PAI-1 of the present invention. The term "salts" refers to both salts of carboxyl groups and to acid addition salts of amino groups of the protein or peptide. Salts of a carboxyl group include inorganic salts, for example, sodium, calcium, ammonium, ferric or zinc salts, and the like, and salts with organic bases such as those formed with amines, such as triethanolamine, arginine, or lysine, piperidine, procaine, and the like. Acid addition salts include salts with mineral acids such as hydrochloric or sulfuric acid, and salts with organic acids such as acetic or oxalic acid.

The pharmaceutical preparations of the present invention are manufactured in a manner which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension.

The pharmaceutical formulation for systemic administration according to the invention may be formulated for enteral, parenteral or topical administration, and all three types of formulation may be used simultaneously to achieve systemic administration of the active ingredient.

As described for lung instillation, aerosolized solutions are used. In a sprayable aerosol preparations, the active purified PAI-1 of the invention may be administered in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

For topical application, the purified PAI-1 of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like. One particularly preferred cream is described below.

Other pharmaceutically acceptable carriers for the purified PAI-1 made in accordance with the present invention are liposomes, pharmaceutical compositions in which the active PAI-1 is contained either dispersed or variously present in corpuscles consisting of aqueous concentric layers adherent to lipidic layers. The active PAI-1 is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

As will be appreciated by the skilled artisan, the purified PAI-1s of the present invention may be useful for treating a variety of lung disorders, including, but not limited to acute respiratory distress syndrome (ARDS) both of the adult variety and the neonatal form, emphysema, cystic fibrosis, CF. Mutant PAI-1s useful for treating lung disorders can be administered parenterally at a dose range of about 10–200 mg/kg/wk.

In addition, the purified PAI-1s of the present invention may be useful for treating periodontal disease and atopic dermatitis (AD), which affects both children and adults.

Periodontal disease is treated preferably by topical application of purified mutant PAI-1 made in accordance with the invention, or alternatively, by systemic therapy. AD is treated by topical administration of a purified mutant PAI-1. Effective doses for both diseases range from about 1 to about 100 mg/ml, preferably about 20–50 mg/ml of purified mutant PAI-1 in aqueous solution given on an alternate days schedule.

Compositions comprising purified PAI-1 of the present invention may also be useful to inhibit HIV-1 infection or to treat individuals having HIV-1.

Other diseases which may be treated by the purified PAI-1s of the present invention include atherosclerosis, restenosis, to inhibit both local and metastatic tumor growth by inhibiting angiogenesis, and thrombosis.

Although the present invention has been described with reference to certain preferred embodiments, various modifications, alterations, and substitutions will be apparent to those skilled in the art without departing from the spirit and scope of the invention, as defined by the appended claims.

EXAMPLES

Example 1

Preparation of Cellular Lysates

The PAI-1 mutant, 14-1b, was expressed in *E. coli* and crude lysates were prepared by standard techniques. The lysates contained EDTA, which interferes with metal binding, and had to be removed prior to applying the lysates to the metal chelating resins. An ammonium sulfate precipitation was employed to remove the EDTA by adding 0.4 grams solid Ammonium sulfate per ml of lysate. The lysate was centrifuged and the pellet collected, making sure that all of the liquid was removed using a paper towel. The pellet was resuspended in the original volume in 50 mM monobasic Sodium phosphate, 100 mM NaCl, pH 6.6. The Ammonium sulfate precipitation was repeated a second time.

Example 2

Purification of PAI-1

The lysates were then applied to 1.0 ml pre-packed HiTrap™ Chelating HP columns (Amersham Pharmacia Biotech, Inc.; Piscataway, N.J.) which were charged with 2 ml of 100 mM cobalt, nickel, copper, zinc or manganese, washed with 5 ml water, and equilibrated with 10 ml of 50 mM monobasic Sodium phosphate, 100 mM NaCl, pH 6.6. Then, 1.5 ml of lysate was applied to the columns. After the lysates were applied to the column, the column was washed with the same buffer used to equilibrate the column. The column was eluted by running an imidazole gradient as described further below.

PAI-1 eluted from the cobalt resin at an imidazole concentration of between 60 and 150 mM. Contaminants were mostly removed in the wash step prior to the imidazole gradient elution. PAI-1 eluted in a single peak and was approximately 98% pure (see FIG. 1). Purity was estimated based on the number of contaminants visible when the peak samples were subjected to SDS-Page gel chromatography.

Figure 2:
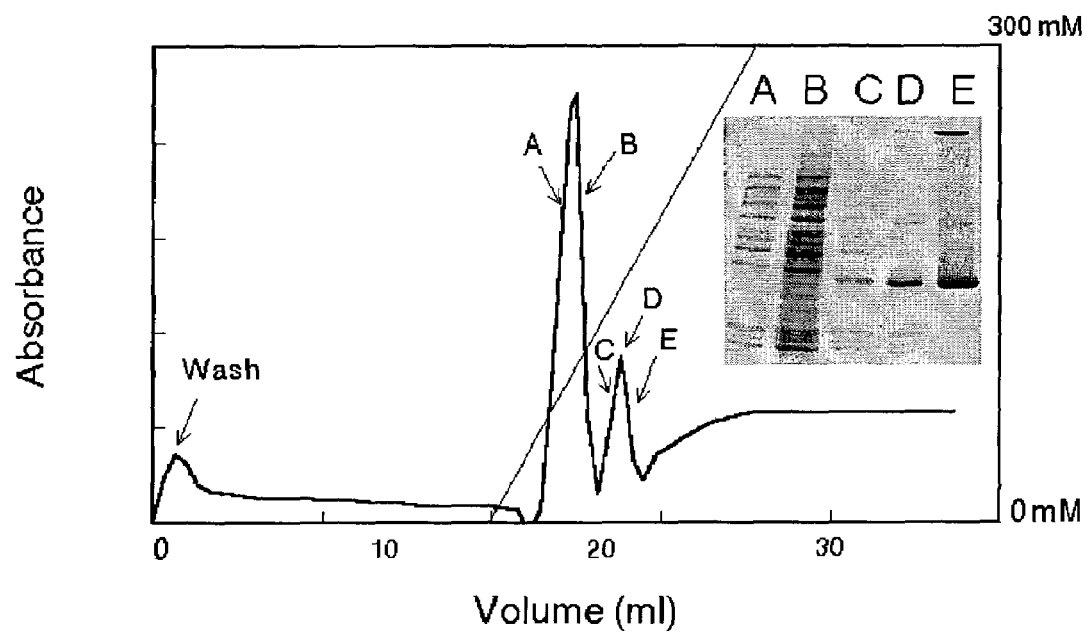
FIG. 2 is a graph showing the elution profile of 14-1b mutant PAI-1 from a nickel HiTrap™ metal chelating column and further showing SDS-PAGE gel electrophoresis of fractions A, B, C, D and E from the major elution peak and shoulder.

PAI-1 eluted from the nickel resin at an imidazole concentration of between 174–240 mM. Two peaks appeared in the imidazole gradient elution step (see FIG. 2). The first peak, which contained the majority of contaminants, eluted at an imidazole concentration of between 78–174 mM. FIG. 2. PAI-1 purified from the nickel resin was about 70% pure (see FIG. 2).

Figure 3:
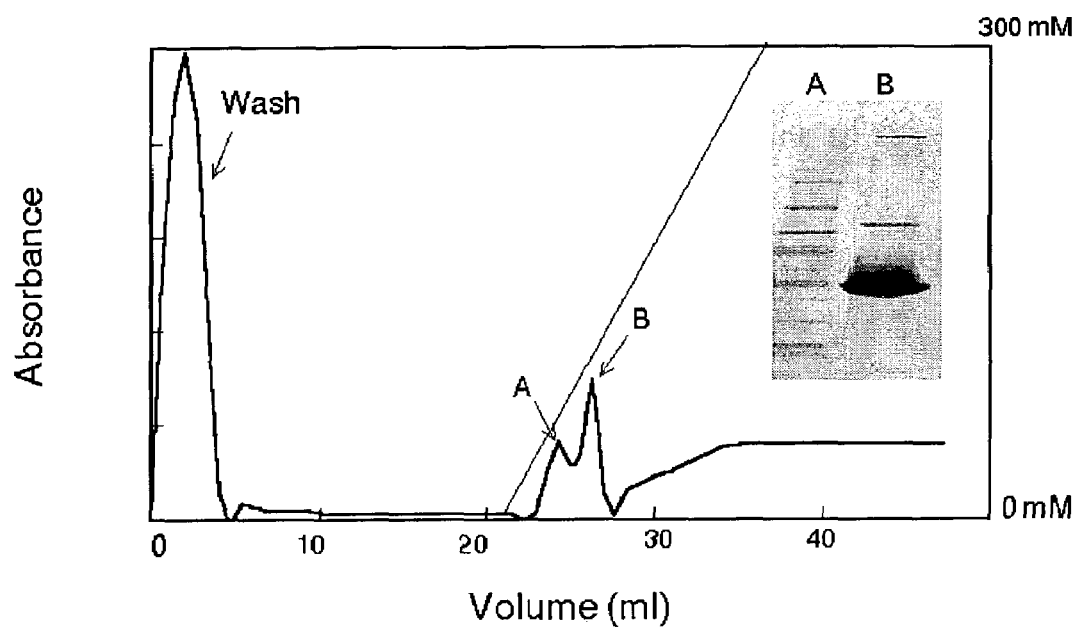
FIG. 3 is a graph showing the elution profile of 14-1b mutant PAI-1 from a zinc HiTrap™ metal chelating column and further showing SDS-PAGE gel electrophoresis of fractions A and B from the major elution peak and shoulder.

PAI-1 eluted from the zinc resin at an imidazole concentration of between 105–150 mM. With the zinc resin, two peaks also appeared in the imidazole gradient elution step (see FIG. 3). The first peak containing the majority of contaminants eluted at an imidazole concentration of between 54–105 mM (FIG. 3). PAI-1 purified from the zinc resin was about 90% pure (see FIG. 3).

Figure 4:
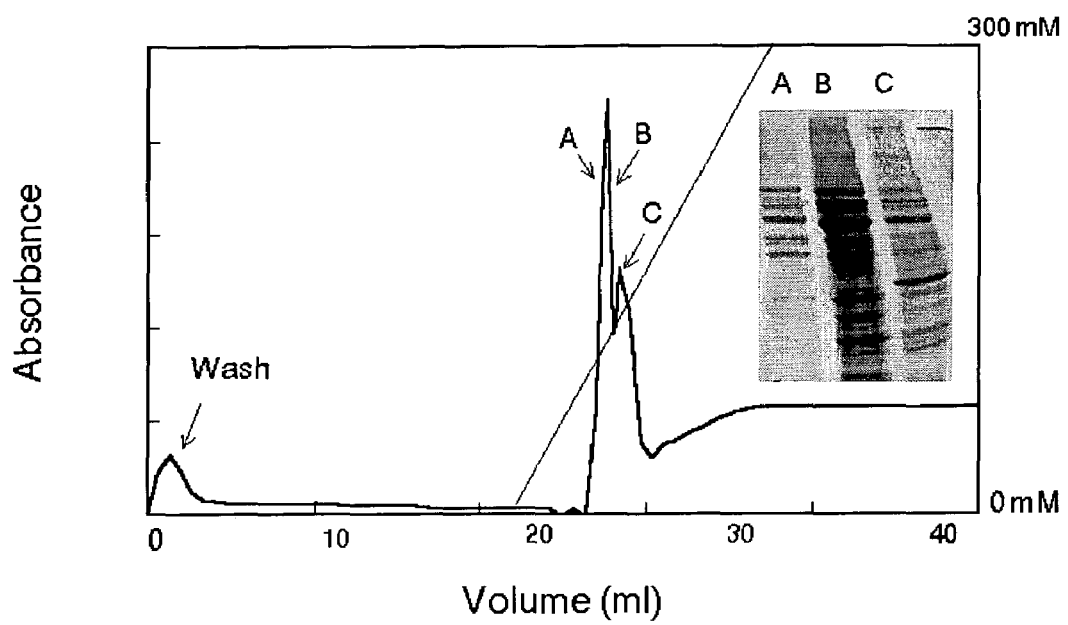
FIG. 4 is a graph showing the elution profile of 14-1b mutant PAI-1 from a copper HiTrap™ metal chelating column and further showing SDS-PAGE gel electrophoresis of fractions A, B and C from the major elution peak and shoulder.
Figure 5:
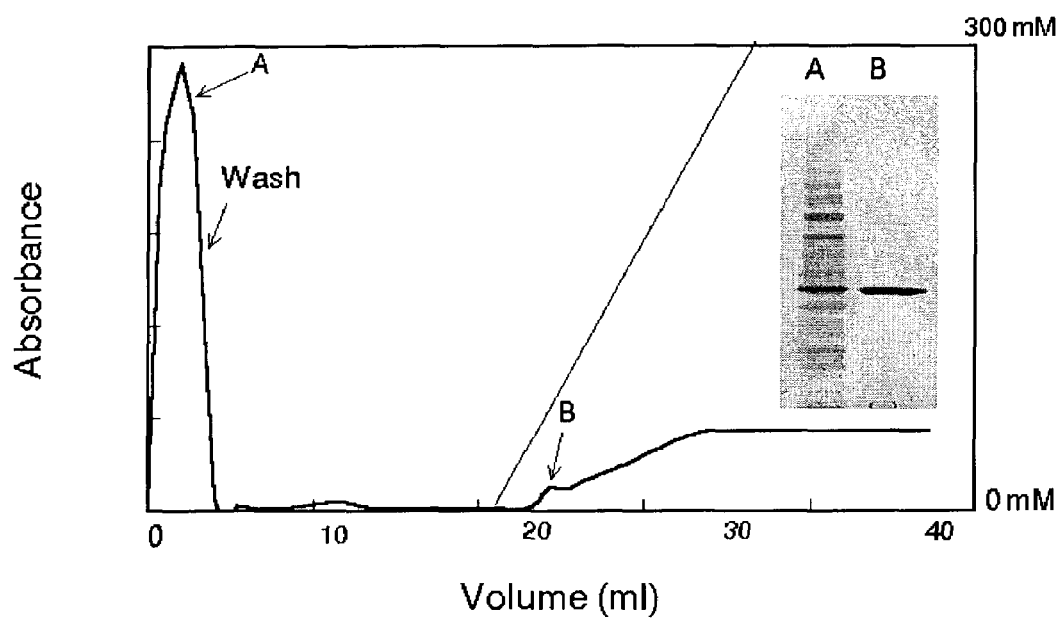
FIG. 5 is a graph showing the elution profile of 14-1b mutant PAI-1 from a manganese HiTrap™ metal chelating column and further showing SDS-PAGE gel electrophoresis of fractions A and B from the wash and the major elution peak.

PAI-1 was also subjected to purification with copper resin and manganese resin. These two resins were not as effective for purifying PAI-1. For the copper resin, PAI-1 eluted at an imidazole concentration from between 138–210 MM, with contaminants eluting from between 78–159 mM (see FIG. 4). The contaminants were not as efficiently removed as they were with the cobalt, nickel and zinc resins (FIG. 4). Therefore, the resultant purified PAI-1 was about 40–50% pure (see FIG. 4). For the manganese resin, the PAI did not bind efficiently and most of it flowed through the column. The small amount that did bind eluted at approximately 84 mM (see FIG. 5).

Figure 6:
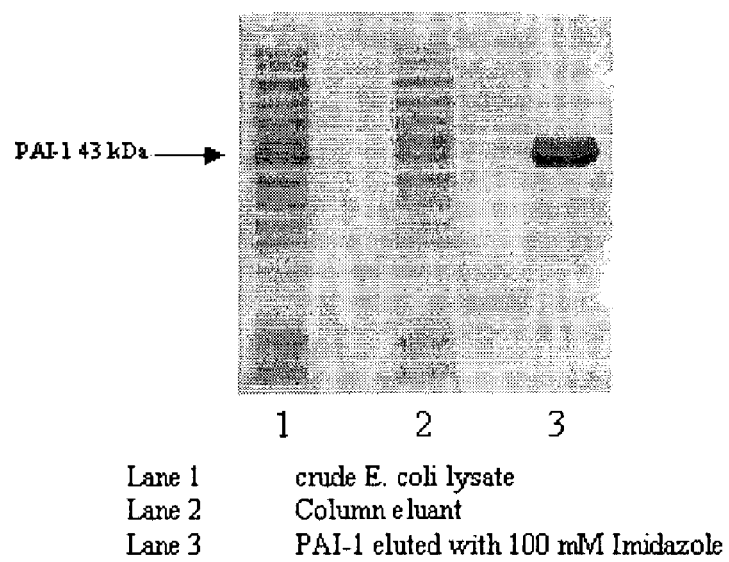
FIG. 6 shows the SDS-PAGE gel electrophoresis of the crude lysate, column wash (eluant) and elution of wild type PAI-1 from a cobalt Talon metal chelating column.

Wild-type PAI-1 was also purified according to the present invention as described above. However, a Talon cobalt metal chelating resin (BD Biosciences Clontech; Palo Alto, Calif.) was used. FIG. 6 shows the crude lysate (lane 1), the wash (eluant; lane 2) of the column and the elution of the column (lane 3) with 100 mM imidizole.

What is claimed is:

1. A method for purifying Plasminogen Activator-Inhibitor type 1 (PAI1) comprising: (a) subjecting unpurified PAI-1 to a solid support comprising a divalent metal selected from the group consisting of nickel and cobalt, wherein the PAI-1 binds to the solid support; and (b) eluting the PAI-1 from the solid support to produce purified PAI-1, wherein the PAI-1 does not comprise a six histidine tag.

2. A method for purifying PAI-1 consisting essentially of: (a) subjecting unpurified PAI-1 to a solid support comprising a divalent metal, wherein the PAI-1 binds to the solid support; and (b) eluting the PAI-1 from the solid support to produce purified PAI-1, wherein the PAI-1 does not comprise a six histidine tag, and wherein the purified PAI-1 is from about 70% to about 100% pure.

3. The method of claim 1 or 2 wherein the PAI-1 is selected from the group consisting of wild-type PAI-1, mutant PAI-1, and fragments thereof.

4. The method of claim 1 or 2 wherein the unpurified PAI-1 is selected from the group consisting of a cellular extract comprising endogenous PAI-1, a cellular extract comprising recombinant PAI-1, and a biochemical reaction.

5. The method of claim 1 wherein the purified PAI-1 is from about 70% to about 100% pure.

6. The method of claim 1 or 2 wherein the purified PAI-1 is from about 85% to about 98% pure.

7. The method of claim 2 wherein the solid support comprising a divalent metal is a resin comprising a divalent metal selected from the group consisting of cobalt, nickel and zinc.

* * * * *